United States Patent
Goldman et al.

(10) Patent No.: US 10,813,588 B2
(45) Date of Patent: *Oct. 27, 2020

(54) MICRO VEIN ENHANCER

(71) Applicant: AccuVein, Inc., Cold Spring Harbor, NY (US)

(72) Inventors: Ron Goldman, Cold Spring Harbor, NY (US); David Hunt, Cincinnati, OH (US); Mark Mock, Covington, KY (US); Graham Marshall, Shoreham, NY (US); Stephen P. Conlon, Cold Spring Harbor, NY (US); Robert H. Roth, Cincinnati, OH (US)

(73) Assignee: AccuVein, Inc., Medford, NY (US)

( * ) Notice: Subject to any disclaimer, the term of this patent is extended or adjusted under 35 U.S.C. 154(b) by 1006 days.

This patent is subject to a terminal disclaimer.

(21) Appl. No.: 14/249,462

(22) Filed: Apr. 10, 2014

(65) Prior Publication Data
US 2015/0289801 A1   Oct. 15, 2015
US 2017/0156660 A9   Jun. 8, 2017

Related U.S. Application Data

(63) Continuation of application No. 13/444,940, filed on Apr. 12, 2012, now Pat. No. 8,750,970, which is a (Continued)

(51) Int. Cl.
| | |
|---|---|
| *A61B 5/00* | (2006.01) |
| *A61M 5/42* | (2006.01) |
| *A61B 5/15* | (2006.01) |

(52) U.S. Cl.
CPC ........... *A61B 5/489* (2013.01); *A61B 5/0075* (2013.01); *A61B 5/0082* (2013.01); *A61B 5/150748* (2013.01); *A61M 5/427* (2013.01)

(58) Field of Classification Search
None
See application file for complete search history.

(56) References Cited

U.S. PATENT DOCUMENTS

| | | | |
|---|---|---|---|
| 3,136,310 | A | 6/1964 | Meltzer |
| 3,349,762 | A | 10/1967 | Kapany |
| (Continued) | | | |

FOREIGN PATENT DOCUMENTS

| | | |
|---|---|---|
| FR | 2289149 | 5/1976 |
| GB | 1298707 | 12/1972 |
| (Continued) | | |

OTHER PUBLICATIONS

Wiklof, Chris, "Display Technology Spawns Laser Camera," LaserFocusWorld, Dec. 1, 2004, vol. 40, Issue 12, PennWell Corp., USA.

(Continued)

*Primary Examiner* — James M Kish
(74) *Attorney, Agent, or Firm* — Thomas A. O'Rourke; Bodner + O'Rourke, LLP

(57) ABSTRACT

The present invention is a Miniature Vein Enhancer that includes a Miniature Projection Head. The Miniature Projection Head may be operated in one of three modes, AFM, DBM, and RTM. The Miniature Projection Head of the present invention projects an image of the veins of a patient, which aids the practitioner in pinpointing a vein for an intravenous drip, blood test, and the like. The Miniature projection head may have a cavity for a power source or it may have a power source located in a body portion of the Miniature Vein Enhancer. The Miniature Vein Enhancer may be attached to one of several improved needle protectors, or the Miniature Vein Enhancer may be attached to a body similar to a flashlight for hand held use. The Miniature Vein (Continued)

Enhancer of the present invention may also be attached to a magnifying glass, a flat panel display, and the like.

25 Claims, 8 Drawing Sheets

Related U.S. Application Data continuation of application No. 11/985,343, filed on Nov. 14, 2007, now Pat. No. 8,255,040, which is a continuation-in-part of application No. 11/700,729, filed on Jan. 31, 2007, now Pat. No. 8,838,210, and a continuation-in-part of application No. 11/478,322, filed on Jun. 29, 2006, now Pat. No. 8,478,386.

(60) Provisional application No. 60/817,623, filed on Jun. 29, 2006, provisional application No. 60/757,704, filed on Jan. 10, 2006.

(56) References Cited

U.S. PATENT DOCUMENTS

| | | | |
|---|---|---|---|
| 3,511,227 A | 5/1970 | Johnson | |
| 3,527,932 A | 9/1970 | Thomas | |
| 3,818,129 A | 6/1974 | Yamamoto | |
| 3,984,629 A | 10/1976 | Gorog | |
| 4,030,209 A | 6/1977 | Dreiding | |
| 4,057,784 A | 11/1977 | Tafoya | |
| 4,109,647 A | 8/1978 | Stern et al. | |
| 4,162,405 A | 7/1979 | Chance et al. | |
| 4,182,322 A | 1/1980 | Miller | |
| 4,185,808 A | 1/1980 | Donohoe et al. | |
| 4,213,678 A | 7/1980 | Pomerantzeff et al. | |
| 4,265,227 A | 5/1981 | Ruge | |
| 4,312,357 A | 1/1982 | Andersson et al. | |
| 4,315,318 A | 2/1982 | Kato et al. | |
| 4,321,930 A | 3/1982 | Jobsis et al. | |
| 4,393,366 A | 7/1983 | Hill | |
| 4,495,949 A | 1/1985 | Stoller | |
| 4,502,075 A | 2/1985 | DeForest et al. | |
| 4,510,938 A | 4/1985 | Jobsis et al. | |
| 4,536,790 A | 8/1985 | Kruger et al. | |
| 4,565,968 A | 1/1986 | Macovski | |
| 4,567,896 A | 2/1986 | Barnea et al. | |
| 4,576,175 A | 3/1986 | Epstein | |
| 4,586,190 A | 4/1986 | Tsuji | |
| 4,590,948 A | 5/1986 | Nilsson | |
| 4,596,254 A | 6/1986 | Adrian et al. | |
| 4,619,249 A | 10/1986 | Landry | |
| 4,669,467 A | 6/1987 | Willett et al. | |
| 4,697,147 A | 9/1987 | Moran et al. | |
| 4,699,149 A | 10/1987 | Rice | |
| 4,703,758 A | 11/1987 | Omura | |
| 4,766,299 A | 8/1988 | Tierney et al. | |
| 4,771,308 A | 9/1988 | Tejima et al. | |
| 4,780,919 A | 11/1988 | Harrison | |
| 4,799,103 A | 1/1989 | Muckerheide | |
| 4,817,622 A | 4/1989 | Pennypacker et al. | |
| 4,846,183 A | 7/1989 | Martin | |
| 4,861,973 A | 8/1989 | Hellekson et al. | |
| 4,862,894 A | 9/1989 | Fujii | |
| 4,899,756 A | 2/1990 | Sonek | |
| 4,901,019 A | 2/1990 | Wedeen | |
| 4,926,867 A | 5/1990 | Kanda et al. | |
| RE33,234 E | 6/1990 | Landry | |
| 4,938,205 A | 7/1990 | Nudelman | |
| 5,074,642 A | 12/1991 | Hicks | |
| 5,088,493 A | 2/1992 | Giannini et al. | |
| 5,103,497 A | 4/1992 | Hicks | |
| 5,146,923 A | 9/1992 | Dhawan | |
| 5,174,298 A | 12/1992 | Dolfi et al. | |
| 5,184,188 A | 2/1993 | Bull et al. | |
| 5,214,458 A | 5/1993 | Kanai | |
| 5,222,495 A | 6/1993 | Clarke et al. | |
| 5,261,581 A | 11/1993 | Harden, Sr. | |
| 5,293,873 A | 3/1994 | Fang | |
| 5,339,817 A | 8/1994 | Nilsson | |
| 5,371,347 A | 12/1994 | Plesko | |
| 5,406,070 A | 4/1995 | Edgar et al. | |
| 5,418,546 A | 5/1995 | Nakagakiuchi et al. | |
| 5,423,091 A | 6/1995 | Lange | |
| 5,436,655 A | 7/1995 | Hiyama et al. | |
| 5,445,157 A | 8/1995 | Adachi et al. | |
| 5,455,157 A | 8/1995 | Adachi | |
| D362,910 S | 10/1995 | Creaghan | |
| 5,485,530 A | 1/1996 | Lakowicz et al. | |
| 5,487,740 A | 1/1996 | Sulek et al. | |
| 5,494,032 A | 2/1996 | Robinson et al. | |
| 5,497,769 A | 3/1996 | Gratton et al. | |
| 5,501,680 A * | 3/1996 | Kurtz | A61B 18/203 606/10 |
| 5,504,316 A | 4/1996 | Bridgelall et al. | |
| 5,519,208 A | 5/1996 | Esparza et al. | |
| 5,541,820 A | 7/1996 | McLaughlin | |
| 5,542,421 A | 8/1996 | Erdman | |
| 5,543,866 A * | 8/1996 | Van de Velde | A61B 3/1025 351/205 |
| 5,598,842 A | 2/1997 | Ishihara et al. | |
| 5,603,328 A | 2/1997 | Zucker et al. | |
| 5,608,210 A | 3/1997 | Esparza et al. | |
| 5,610,387 A | 3/1997 | Bard et al. | |
| 5,625,458 A | 4/1997 | Alfano et al. | |
| 5,631,976 A | 5/1997 | Bolle et al. | |
| 5,655,530 A | 8/1997 | Messerschmidt | |
| 5,678,555 A | 10/1997 | O'Connell | |
| 5,716,796 A | 2/1998 | Bull et al. | |
| 5,719,399 A | 2/1998 | Alfano et al. | |
| 5,740,801 A | 4/1998 | Branson | |
| 5,747,789 A | 5/1998 | Godik | |
| 5,749,830 A * | 5/1998 | Kaneko | A61B 1/00082 348/E5.038 |
| 5,756,981 A | 5/1998 | Roustaei et al. | |
| 5,758,650 A | 6/1998 | Miller et al. | |
| 5,772,593 A | 6/1998 | Hakamata | |
| 5,784,148 A * | 7/1998 | Heacock | A61B 3/1025 351/206 |
| 5,787,185 A | 7/1998 | Clayden | |
| 5,814,040 A | 9/1998 | Nelson et al. | |
| 5,836,877 A | 11/1998 | Zavislan | |
| 5,847,394 A | 12/1998 | Alfano et al. | |
| 5,860,967 A | 1/1999 | Zavislan et al. | |
| 5,929,443 A | 7/1999 | Alfano et al. | |
| 5,946,220 A | 8/1999 | Lemelson | |
| 5,947,906 A | 9/1999 | Dawson, Jr. et al. | |
| 5,966,204 A | 10/1999 | Abe | |
| 5,966,230 A | 10/1999 | Swartz et al. | |
| 5,969,754 A | 10/1999 | Zeman | |
| 5,982,553 A * | 11/1999 | Bloom | G02B 5/1828 359/627 |
| 5,988,817 A | 11/1999 | Mizushima et al. | |
| 5,995,856 A | 11/1999 | Mannheimer et al. | |
| 5,995,866 A | 11/1999 | Lemelson | |
| 6,006,126 A | 12/1999 | Cosman | |
| 6,032,070 A | 2/2000 | Flock et al. | |
| 6,056,692 A | 5/2000 | Schwartz | |
| 6,061,583 A | 5/2000 | Ishihara et al. | |
| 6,083,486 A | 7/2000 | Weissleder et al. | |
| 6,101,036 A | 8/2000 | Bloom | |
| 6,113,536 A | 9/2000 | Aboul-Hosn et al. | |
| 6,122,042 A | 9/2000 | Wunderman et al. | |
| 6,132,379 A | 10/2000 | Patacsil et al. | |
| 6,135,599 A | 10/2000 | Fang | |
| 6,141,985 A | 11/2000 | Cluzeau et al. | |
| 6,142,650 A | 11/2000 | Brown et al. | |
| 6,149,061 A | 11/2000 | Massieu et al. | |
| 6,149,644 A | 11/2000 | Xie | |
| 6,171,301 B1 | 1/2001 | Nelson et al. | |
| 6,178,340 B1 * | 1/2001 | Svetliza | A61B 5/0059 250/226 |
| 6,179,260 B1 | 1/2001 | Ohanian | |
| 6,230,046 B1 | 5/2001 | Crane et al. | |
| 6,240,309 B1 | 5/2001 | Yamashita et al. | |
| 6,251,073 B1 | 6/2001 | Imran et al. | |

(56) References Cited

U.S. PATENT DOCUMENTS

| | | |
|---|---|---|
| 6,263,227 B1 | 7/2001 | Boggett et al. |
| 6,272,376 B1 | 8/2001 | Marcu et al. |
| 6,301,375 B1 | 10/2001 | Choi |
| 6,305,804 B1 | 10/2001 | Rice et al. |
| 6,314,311 B1 | 11/2001 | Williams et al. |
| 6,334,850 B1 | 1/2002 | Amano et al. |
| 6,353,753 B1 | 3/2002 | Flock et al. |
| 6,424,858 B1 | 7/2002 | Williams |
| 6,436,655 B1 | 8/2002 | Bull et al. |
| 6,438,396 B1 | 8/2002 | Cook et al. |
| 6,463,309 B1 | 10/2002 | Ilia |
| 6,464,646 B1 | 10/2002 | Shalom et al. |
| 6,523,955 B1 | 2/2003 | Eberl et al. |
| 6,542,246 B1 | 4/2003 | Toida |
| 6,556,854 B1 | 4/2003 | Sato et al. |
| 6,556,858 B1 * | 4/2003 | Zeman ............... A61B 5/0059 250/330 |
| 6,599,247 B1 | 7/2003 | Stetten |
| 6,631,286 B2 | 10/2003 | Pfeiffer et al. |
| 6,648,227 B2 | 11/2003 | Swartz et al. |
| 6,650,916 B2 | 11/2003 | Cook et al. |
| 6,689,075 B2 | 2/2004 | West |
| 6,690,964 B2 | 2/2004 | Bieger et al. |
| 6,702,749 B2 | 3/2004 | Paladini et al. |
| 6,719,257 B1 | 4/2004 | Greene et al. |
| 6,755,789 B2 | 6/2004 | Stringer et al. |
| 6,777,199 B2 | 8/2004 | Bull et al. |
| 6,782,161 B2 | 8/2004 | Barolet et al. |
| 6,845,190 B1 | 1/2005 | Smithwick et al. |
| 6,882,875 B1 | 4/2005 | Crowley |
| 6,889,075 B2 | 5/2005 | Marchitto et al. |
| 6,913,202 B2 | 7/2005 | Tsikos et al. |
| 6,923,762 B1 | 8/2005 | Creaghan, Jr. |
| 6,980,852 B2 | 12/2005 | Jersey-Willuhn et al. |
| 7,092,087 B2 | 8/2006 | Kumar et al. |
| 7,113,817 B1 | 9/2006 | Winchester, Jr. et al. |
| 7,158,660 B2 | 1/2007 | Gee, Jr. et al. |
| 7,158,859 B2 | 1/2007 | Wang et al. |
| 7,204,424 B2 | 4/2007 | Yavid et al. |
| 7,225,005 B2 | 5/2007 | Kaufman et al. |
| 7,227,611 B2 | 6/2007 | Hull et al. |
| 7,239,909 B2 | 7/2007 | Zeman |
| 7,247,832 B2 | 7/2007 | Webb |
| 7,280,860 B2 | 10/2007 | Ikeda et al. |
| 7,283,181 B2 | 10/2007 | Allen et al. |
| 7,302,174 B2 | 11/2007 | Tan et al. |
| 7,333,213 B2 | 2/2008 | Kempe |
| D566,283 S | 4/2008 | Brafford et al. |
| 7,359,531 B2 | 4/2008 | Endoh et al. |
| 7,376,456 B2 | 5/2008 | Marshik-Geurts et al. |
| 7,428,997 B2 | 9/2008 | Wiklof et al. |
| 7,431,695 B1 | 10/2008 | Creaghan |
| 7,448,995 B2 | 11/2008 | Wiklof et al. |
| 7,532,746 B2 | 5/2009 | Marcotte et al. |
| 7,545,837 B2 | 6/2009 | Oka |
| 7,559,895 B2 | 7/2009 | Stetten et al. |
| 7,579,592 B2 | 8/2009 | Kaushal |
| 7,608,057 B2 | 10/2009 | Woehr et al. |
| 7,699,776 B2 | 4/2010 | Walker et al. |
| 7,708,695 B2 | 5/2010 | Akkermans et al. |
| 7,792,334 B2 | 9/2010 | Cohen et al. |
| 7,846,103 B2 | 12/2010 | Cannon, Jr. et al. |
| 7,848,103 B2 | 12/2010 | Zhan |
| 7,904,138 B2 | 3/2011 | Goldman et al. |
| 7,904,139 B2 | 3/2011 | Chance |
| 7,925,332 B2 | 4/2011 | Crane et al. |
| 7,966,051 B2 | 6/2011 | Xie et al. |
| 8,032,205 B2 | 10/2011 | Mullani |
| 8,078,263 B2 | 12/2011 | Zeman et al. |
| 8,187,189 B2 | 5/2012 | Jung et al. |
| 8,199,189 B2 | 6/2012 | Kagenow et al. |
| 8,320,998 B2 | 11/2012 | Sato |
| 8,336,839 B2 | 12/2012 | Boccoleri et al. |
| 8,364,246 B2 | 1/2013 | Thierman |
| 8,467,855 B2 | 6/2013 | Yasui |
| 8,480,662 B2 | 7/2013 | Stolen et al. |
| 8,494,616 B2 | 7/2013 | Zeman |
| 8,498,694 B2 | 7/2013 | McGuire, Jr. et al. |
| 8,509,495 B2 | 8/2013 | Xu et al. |
| 8,537,203 B2 | 9/2013 | Seibel et al. |
| 8,548,572 B2 | 10/2013 | Crane |
| 8,630,465 B2 | 1/2014 | Wieringa et al. |
| 8,649,848 B2 | 2/2014 | Crane et al. |
| 2001/0006426 A1 | 7/2001 | Son et al. |
| 2001/0056237 A1 | 12/2001 | Cane et al. |
| 2002/0016533 A1 | 2/2002 | Marchitto et al. |
| 2002/0111546 A1 | 8/2002 | Cook |
| 2002/0118338 A1 | 8/2002 | Kohayakawa |
| 2002/0188203 A1 | 12/2002 | Smith et al. |
| 2003/0018271 A1 | 1/2003 | Kimble |
| 2003/0037375 A1 | 2/2003 | Riley et al. |
| 2003/0047683 A1 * | 3/2003 | Kaushal ............... G02B 23/12 250/330 |
| 2003/0052105 A1 | 3/2003 | Nagano et al. |
| 2003/0120154 A1 | 6/2003 | Sauer et al. |
| 2003/0125629 A1 | 7/2003 | Ustuner |
| 2003/0156260 A1 | 8/2003 | Putilin et al. |
| 2004/0015062 A1 | 1/2004 | Ntziachristos et al. |
| 2004/0015158 A1 | 1/2004 | Chen et al. |
| 2004/0022421 A1 | 2/2004 | Endoh et al. |
| 2004/0046031 A1 | 3/2004 | Knowles et al. |
| 2004/0171923 A1 * | 9/2004 | Kalafut ............... A61B 5/0059 600/407 |
| 2004/0222301 A1 | 11/2004 | Willins et al. |
| 2004/0237051 A1 | 11/2004 | Clauson |
| 2005/0017924 A1 | 1/2005 | Utt et al. |
| 2005/0033145 A1 | 2/2005 | Graham et al. |
| 2005/0043596 A1 | 2/2005 | Chance |
| 2005/0047134 A1 | 3/2005 | Mueller et al. |
| 2005/0085732 A1 | 4/2005 | Sevick-Muraca et al. |
| 2005/0085802 A1 | 4/2005 | Gruzdev et al. |
| 2005/0113650 A1 | 5/2005 | Pacione et al. |
| 2005/0131291 A1 | 6/2005 | Floyd et al. |
| 2005/0135102 A1 | 6/2005 | Gardiner et al. |
| 2005/0141069 A1 | 6/2005 | Wood et al. |
| 2005/0143662 A1 | 6/2005 | Marchitto et al. |
| 2005/0146765 A1 | 7/2005 | Turner et al. |
| 2005/0154303 A1 | 7/2005 | Walker et al. |
| 2005/0157939 A1 | 7/2005 | Arsenault et al. |
| 2005/0161051 A1 | 7/2005 | Pankratov et al. |
| 2005/0168980 A1 | 8/2005 | Dryden et al. |
| 2005/0174777 A1 | 8/2005 | Cooper et al. |
| 2005/0175048 A1 | 8/2005 | Stern et al. |
| 2005/0187477 A1 | 8/2005 | Serov et al. |
| 2005/0215875 A1 | 9/2005 | Khou |
| 2005/0265586 A1 | 12/2005 | Rowe et al. |
| 2005/0281445 A1 | 12/2005 | Marcotte et al. |
| 2006/0007134 A1 | 1/2006 | Ting |
| 2006/0020212 A1 | 1/2006 | Xu et al. |
| 2006/0025679 A1 | 2/2006 | Viswanathan et al. |
| 2006/0052690 A1 | 3/2006 | Sirohey et al. |
| 2006/0081252 A1 | 4/2006 | Wood |
| 2006/0100523 A1 | 5/2006 | Ogle et al. |
| 2006/0103811 A1 | 5/2006 | May et al. |
| 2006/0122515 A1 | 6/2006 | Zeman et al. |
| 2006/0129037 A1 | 6/2006 | Kaufman et al. |
| 2006/0129038 A1 | 6/2006 | Zelenchuk et al. |
| 2006/0151449 A1 | 7/2006 | Warner, Jr. et al. |
| 2006/0173351 A1 | 8/2006 | Marcotte et al. |
| 2006/0184040 A1 | 8/2006 | Keller et al. |
| 2006/0206027 A1 | 9/2006 | Malone |
| 2006/0232660 A1 | 10/2006 | Nakajima et al. |
| 2006/0253010 A1 | 11/2006 | Brady et al. |
| 2006/0271028 A1 | 11/2006 | Altshuler et al. |
| 2006/0276712 A1 | 12/2006 | Stothers |
| 2007/0015980 A1 | 1/2007 | Numada et al. |
| 2007/0016079 A1 | 1/2007 | Freeman et al. |
| 2007/0070302 A1 | 3/2007 | Govorkov et al. |
| 2007/0115435 A1 | 5/2007 | Rosendaal |
| 2007/0129634 A1 * | 6/2007 | Hickey ............... F16M 11/18 600/439 |
| 2007/0176851 A1 | 8/2007 | Willey et al. |
| 2007/0238957 A1 | 10/2007 | Yared |
| 2008/0045841 A1 | 2/2008 | Wood et al. |

(56) References Cited

U.S. PATENT DOCUMENTS

| | | |
|---|---|---|
| 2008/0147147 A1 | 6/2008 | Griffiths et al. |
| 2008/0194930 A1 | 8/2008 | Harris et al. |
| 2008/0214940 A1 | 9/2008 | Benaron |
| 2009/0018414 A1 | 1/2009 | Toofan |
| 2009/0082629 A1 | 3/2009 | Dotan |
| 2009/0171205 A1 | 7/2009 | Kharin et al. |
| 2010/0051808 A1 | 3/2010 | Zeman et al. |
| 2010/0061598 A1 | 3/2010 | Seo |
| 2010/0087787 A1 | 4/2010 | Woehr et al. |
| 2010/0177184 A1 | 7/2010 | Berryhill et al. |
| 2010/0312120 A1 | 12/2010 | Meier |
| 2011/0275932 A1 | 11/2011 | Leblond et al. |
| 2013/0147916 A1 | 6/2013 | Bennett et al. |
| 2014/0039309 A1 | 2/2014 | Harris et al. |
| 2014/0046291 A1 | 2/2014 | Harris et al. |
| 2014/0194747 A1 | 7/2014 | Kruglick |

FOREIGN PATENT DOCUMENTS

| | | |
|---|---|---|
| GB | 1507329 | 4/1978 |
| JP | S60-108043 A | 6/1985 |
| JP | 04-042944 | 2/1992 |
| JP | 07-255847 | 10/1995 |
| JP | 08-023501 A | 1/1996 |
| JP | 08023501 A | 1/1996 |
| JP | 08-164123 | 6/1996 |
| JP | 2000/316866 A | 11/2000 |
| JP | 2000-316866 A | 11/2000 |
| JP | 2002 328428 A | 11/2002 |
| JP | 2002-328428 A | 11/2002 |
| JP | 2002-345953 A | 12/2002 |
| JP | 2002/345953 A | 12/2002 |
| JP | 2004 237051 | 8/2004 |
| JP | 2004-237051 | 8/2004 |
| JP | 2004-329786 A | 11/2004 |
| JP | 2004/329786 A | 11/2004 |
| JP | 2006-102360 | 4/2006 |
| KR | 2003/0020152 A | 3/2003 |
| KR | 2003-0020152 A | 3/2003 |
| WO | WO 1994 22370 | 10/1994 |
| WO | WO 96/39925 | 12/1996 |
| WO | WO 1996 39925 | 12/1996 |
| WO | WO 1996 39926 | 12/1996 |
| WO | WO 1998 26583 | 6/1998 |
| WO | WO 9826583 | 6/1998 |
| WO | WO 99/48420 | 9/1999 |
| WO | WO 1999 48420 | 9/1999 |
| WO | WO 2001 82786 | 11/2001 |
| WO | WO 2001-82786 | 11/2001 |
| WO | WO 2003 009750 | 2/2003 |
| WO | WO 2003-009750 | 2/2003 |
| WO | WO 2005-053773 | 6/2005 |
| WO | WO 2005053773 | 6/2005 |
| WO | WO 2007-078447 | 7/2007 |
| WO | WO 2007 078447 | 12/2007 |

OTHER PUBLICATIONS

Nikbin, Darius, "IPMS Targets Colour Laser Projectors," Optics & Laser Europe, Mar. 2006, Issue 137, p. 11.

Nikbin, Darius, "IPMS Targets Colour Laser Projectors," Optics & Laser Europe, March 1006, Isue 137, p. 11.

http://sciencegeekgirl.wordpress.com/category/science-myths/page/2/ Myth 7: Blood is Blue.

http://www.exploratorium.edu/sports/hnds_up/hands6.html "Hands Up! To Do & Notice: Getting the Feel of Your Hand".

http://www.wikihow.com/See-Blook-Veins-in-Your-Hand-With-a-Flashlight "How to See Blood Veins in Your Hand With a Flashlight".

\* cited by examiner

MICRO VEIN ENHANCER

CROSS REFERENCES TO RELATED APPLICATIONS

This application is a continuation of U.S. application Ser. No. 13/444,940, filed on Apr. 12, 2012, which is a continuation of U.S. application Ser. No. 11/985,343, filed on Nov. 14, 2007, now issued as U.S. Pat. No. 8,255,040, which is a continuation-in-part of application Ser. No. 11/478,322, filed on Jun. 29, 2006, now issued as U.S. Pat. No. 8,478, 386, and, also claims priority on provisional patent application entitled Three Dimensional Imaging of Veins, Application No. 60/817,623, also filed on Jun. 29, 2006, all disclosures of which are hereby incorporated by reference.

FIELD OF INVENTION

The invention described herein relates generally to an imaging device, in particular, an imaging means for enhancing visualization of veins, arteries and other subcutaneous structures of the body for facilitating fluid insertion into or extraction from the body or otherwise visualizing subcutaneous structures for diagnosis of the medical condition of a patient or administration of medical treatment to a patient.

BACKGROUND OF THE INVENTION

A visit to a doctor's office, a clinic or a hospital may necessitate vascular access that is, the insertion of a needle or catheter into a patient's vein or artery. These procedures may be required for the following reasons: to administer fluids, drugs or solutions, to obtain and monitor vital signs, to place long-term access devices, and to perform simple venipunctures. Vascular access ranks as the most commonly performed invasive, medical procedure in the U.S—over 1.4 billion procedures annually—as well as the top patient complaint among clinical procedures. The overwhelming majority of vascular access procedures is performed without the aid of any visualization device and relies on what is observed through the patient's skin and by the clinician's ability to feel the vessel. Medical literature reports the following statistics: 28% first attempt IV failure rate in normal adults, 44% first attempt IV failure in pediatrics, 43% of pediatric IVs require three or more insertion attempts, 23% to 28% incidence of extravasations/infiltration, 12% outright failure rate in cancer patients, 25% of hospital in-patients beyond three days encounter difficult access.

It is known in the art to use an apparatus to enhance the visual appearance of the veins in a patient to facilitate insertion of needles into the veins. An example of such a system is described in U.S. Pat. Nos. 5,969,754 and 6,556, 858 incorporated herein by reference as well as a publication entitled "The Clinical Evaluation of Vein Contrast Enhancement". Luminetx is currently marketing such a device under the name "Veinviewer Imaging System" and information related thereto is available on its website, which is incorporated herein by reference.

The Luminetx Vein Contrast Enhancer (hereinafter referred to as LVCE) utilizes an infrared light source for flooding the region to be enhanced with infrared light generated by an array of LEDs. A CCD imager is then used to capture an image of the infrared light reflected off the patient. The resulting captured image is then projected by a visible light projector onto the patient in a position closely aligned with the image capture system. Given that the CCD imager and the image projector are both two dimensional, and do not occupy the same point in space, it is relatively difficult to design and build a system that closely aligns the captured image and the projected image.

A further characteristic of the LVCE is that both the imaging CCD and the projector have fixed focal lengths. Accordingly, the patient must be at a relatively fixed distance relative to the LVCE. This necessitates that the LVCE be positioned at a fixed distance from the region of the patient to be enhanced.

The combination of the size of the LVCE and the fixed focal arrangement precludes using the LVCE as small portable units that are hand held:

Other patents such as U.S. Pat. No. 6,230,046, issued to Crane et al. assigned to The United States of America as represented by the Secretary of the Air Force, implement a light source for illuminating or transilluminating the corresponding portion of the body with light of selected wavelengths and a low-level light detector such as an image intensifier tube (including night vision goggles), a photomultiplier tube, photodiode or charge coupled device, for generating an image of the illuminated body portion, and optical filter(s) of selected spectral transmittance which can be located at the light source(s), detector, or both.

All cited references are incorporated herein by reference in their entireties. Citation of any reference is not an admission regarding any determination as to its availability as prior art to the claimed invention.

SUMMARY OF INVENTION

Finding a vein, necessary for administering intravenous solutions, drips and the like, can often be difficult. During venous penetration, whether for an injection or drip, it is essential to stick a vein in exactly the right location. If a practitioner is only slightly off center, the needle will more then likely just roll off.

The present invention is a Miniature Vein Enhancer that includes a Miniature Projection Head. The Miniature Projection Head of the present invention implements a polarized laser light. This diminishes the effects of specular reflection off the surface of the skin. The Veinviewer Imaging System, produced by Luminetx, uses a polarized filter to polarize the LED light. This polarized LED light is then rotated 90° in front of the camera, thus causing increased power loss.

In addition, the IR and visible lasers in the present invention can be modulated to allow a regular photodiode to detect the different signals from each wavelength separately. Furthermore, the IR laser power of the present invention is dynamically altered during each scan line, thus increasing the working range of the photodiode, and allowing for constant DC gain.

One key feature of the present invention, not present in the prior art, is the use of a hot mirror. A brief description now follows. First, a hot mirror is a specialized dielectric mirror, a dichromatic interference filter often employed to protect optical systems by reflecting heat back into the light source. In addition, hot mirrors can be designed to be inserted into at optical system at an incidence angle varying between zero and 45 degrees. Hot mirrors are useful in a variety of applications where heat build-up can damage components or adversely affect spectral characteristics of the illumination source. These characteristics, although useful in some applications, are not particularly important within the context of the present invention. Generally, wavelengths reflected by an infrared hot mirror range from about 750 to 1250 nanometers. By transmitting visible light wavelengths while reflecting infrared, hot mirrors can also serve as dichromatic beam splitters for specialized applications in fluorescence microscopy, as in the present invention. As mentioned above, hot mirrors are mirrors that may be coated with a Dichroic material, or the like. A Dichroic material is either one which causes visible light to be split up into distinct beams of different wavelengths, or one which light rays having different polarizations are absorbed by different amounts, the former is implemented in the present invention.

The present invention also improves on the Crane Patent. In Crane, the vein enhancer implements two separate devices, one for illumination and/or transillumination and a separate device used for detecting the low light. Such a configuration is awkward and difficult to operate. In addition, having two separate devices increases the likelihood losing one of them.

The present invention can implement multiple photo detectors spatially separated so as to increase sensitivity, reduce speckle, and reduce specular reflection. However, as mentioned previously, one can achieve a reasonable result by using a single PD, this will depend on the desired output and/or operating needs.

The scanning method implemented with the present invention is unique. In general, the lower level of precision required, the easier it is to produce the pattern. In the present invention (the embodiment without image memory), as opposed to a traditional laser projectors known in the art, there is no need for a reproducible scan pattern, that is, from frame to frame the laser scan lines do not need to fall reproducibly upon the scan lines of the prior frame, thus, there is no need to know the instantaneous position of the laser. The reason being, the visible light of the present invention is coaxially aligned to the 740 un laser. The visible light is a function of the received image in real time. Accordingly, whatever location is being imaged is instantaneously being projected.

The present invention also implements a scanner. The scanner of the present invention can include an amplitude modulated circular mirror. In this case a mirror is arranged to run at resonance in a circular or oval pattern. The magnitude of the circle is then amplitude modulated at a rate in excess of 30 Hz (to avoid appearance of flicker). Accordingly, a scan pattern is formed which starts with small concentric circles and grows sequentially larger, until reaching a limit and than collapsing sequentially to the smallest circle. Some advantages of this configuration include: circle and oval scan; mirror and laser spot always moving, hence, no down time; center of image naturally brighter; scan lines per inch can be denser in center; calibration line is outside circle (can be clipped by housing); and operation at resonance means low power.

The miniature vein enhancer of the present invention may be used by a practitioner to locate a vein, particularly useful when trying to locate a vein in the very old or very young. More then fifty percent of attempts to find a vein, in old people, who have a generally high percentage of loose, fatty tissue, and children, who have a generally high percentage of small veins and "puppy fat", are unsuccessful. The present invention is aimed at reducing and/or preventing the discomfort and delay associated with botched attempts to pierce veins for injections and blood tests. In addition, the present invention can cut the time it takes to set up potentially life-saving intravenous drip.

OBJECTS OF THE INVENTION

It is an object of the present invention to make a Miniature Vein Enhancer that is cost effective to manufacture.

It is another object of the present invention to make a Miniature Vein Enhancer that will allow a practitioner pinpoint a vein for intravenous drip, blood tests, and the like.

It is still another object of the present invention to make a Miniature Vein Enhancer that will reduce and/or diminish the amount of botched attempts to pierce a vein.

It is still a further object of the present invention to make a Miniature Vein Enhancer that is easy to operate.

It is another object of the present invention to make a Miniature Vein Enhancer that may be disposed of after use.

It is yet another object of the present invention to make a Miniature Vein Enhancer that may be hand held.

It is still another object of the invention to make a Miniature Vein Enhancer that implements a Miniature Projection Head in Alternating frame mode.

It is yet another object of the present invention to make a Miniature Vein Enhancer that implements a Miniature Projection Head that operates in Dual Buffer Mode.

It is yet another object of the present invention to make a Miniature Vein Enhancer that implements a Miniature Projection Head that operates in Real Time Mode.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

A detailed description of the different configurations of lasers, mirrors, diodes, gain control systems, as well as the different power controls located inside the MPH will now be discussed. A detailed description of the MPH will then follow.

The present invention can be arranged as either a binary system or grayscale system. In a grayscale system, the 740 nm signal received by the PD is simply echoed and re-transmitted by the visible 638 nm laser 201. In this manner, various levels of intensity can be shown. Accordingly, the image of a vein may vary in intensity as a function of the magnitude of signal received. In a binary system, the projected image is either on or off. To determine whether the projected image should be on or off, a comparator with a trip point is placed after the photodiode. If the signal crosses the trip point the output laser 638 nm 201 is turned on and vice versa. There are several ways to set the trip point. For example, a user dial or press button (or any other input means) could be placed on the device, and the user can manually adjust the trip point (essentially making the device more or less sensitive).

Figure 1:
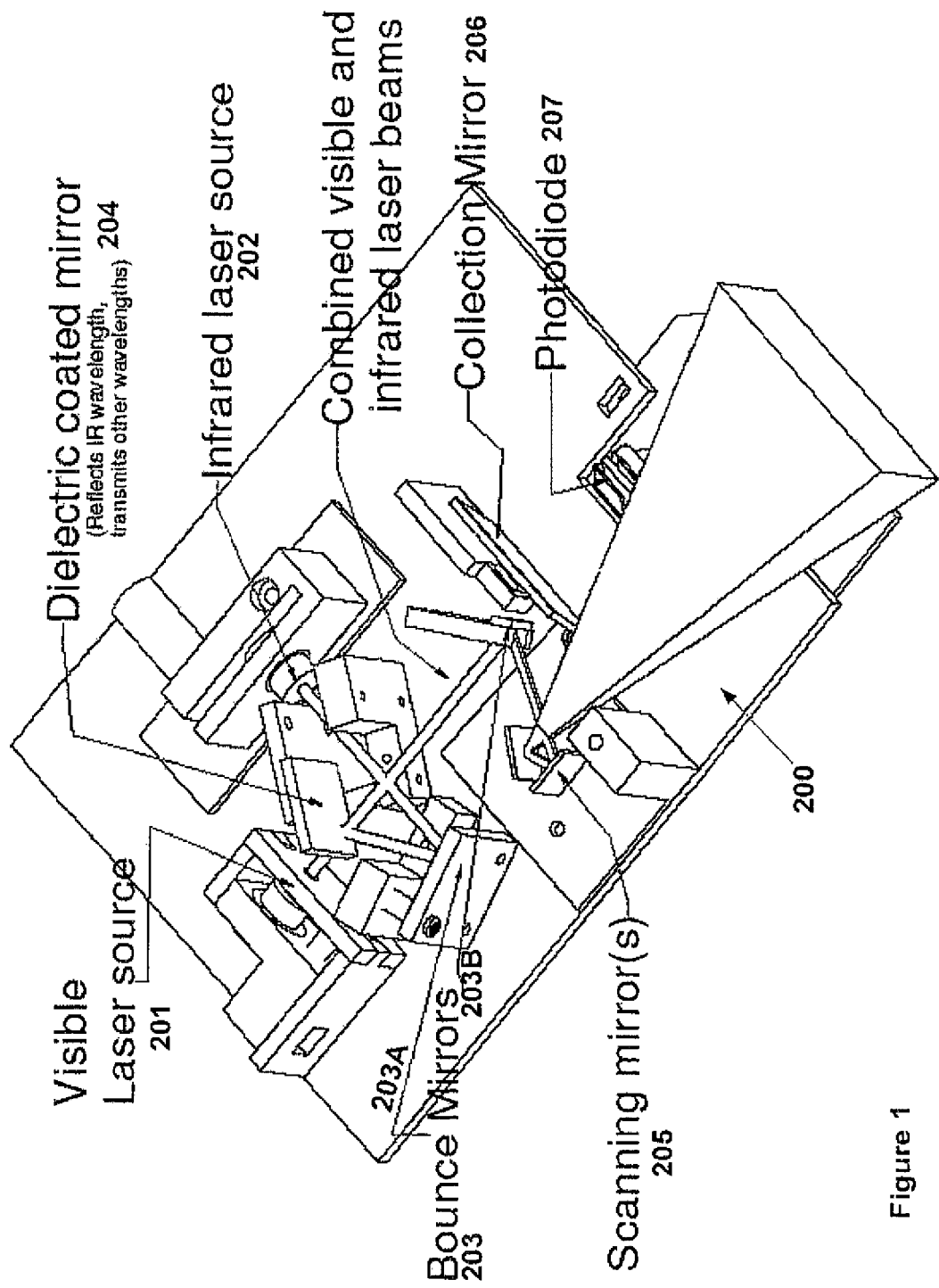
FIG. 1 is a perspective view of the Vein Enhancer of the present invention.

The vein enhancer of the present invention, implements at least two lasers, 201 and 202, contained in the same housing, as seen in FIG. 1, which makes for easier operability and maintainability, that is, less chance of losing one of the devices, as in cited prior art. In addition, the present invention has: improved beam combiner glass, higher power IR, improved mirrors, smaller photo diode setup; used for collection optics, cables for electronic hook-up, AGC, and a microprocessor; used for mirror control and laser calibration. With all the aforementioned enhancements many significant improvements in the vein enhancement art can be obtained, one area in particular, is safety.

Laser projection devices have agency regulations dictating power output limitations. Generally, the power of a laser is limited to a threshold level so as to protect the user's eye from injury. If, however, the user's eye is prevented from getting too close to the laser, then the power of the laser may be increased. Prior art in the past have implemented physical barriers that are incorporated into the design of the laser. These barriers help prevent the user's eye from getting too close to the origin of the laser projections, thus laser power may be increased. For example, previous prior art have used protruding bars (similar to those used in football helmets) that are placed in the direction of the optical path. This prevents the user from placing an eye too close to the laser.

In the present invention, signal processing can be utilized to control the power output. For example, in one embodiment the acquired image pattern is stored in a computer memory. The image is then processed to determine whether veins are present, and only upon confirmation of the vein being present is the image projected. In this manner, the visible laser will not be turned on if the laser is in the direction of the user.

In another embodiment, the power of the 740 nm laser 202 can be set to an initially low setting. Once the laser detects a vein, the power of the 740 nm laser 202 can be increased and the 638 nm laser 201 turned on.

In yet another embodiment, the laser can be configured so that the laser will only be activated when a proximity sensor 220 determines the surface, or eye of a user. The interface of proximity sensor 220 and the main electronics 260 may be seen in FIG. 7.

Although the vein enhancer of the present invention may be configured to operate in a multitude of ways, it includes at least one laser, one photo diode and at least one mirror. Depending on the desired output and/or operating costs additional components may be incorporated into the design of the present invention. Two embodiments that have been found useful in the vein enhancement art will now be discussed, a discussion of alternative embodiments will follow.

Figure 8:
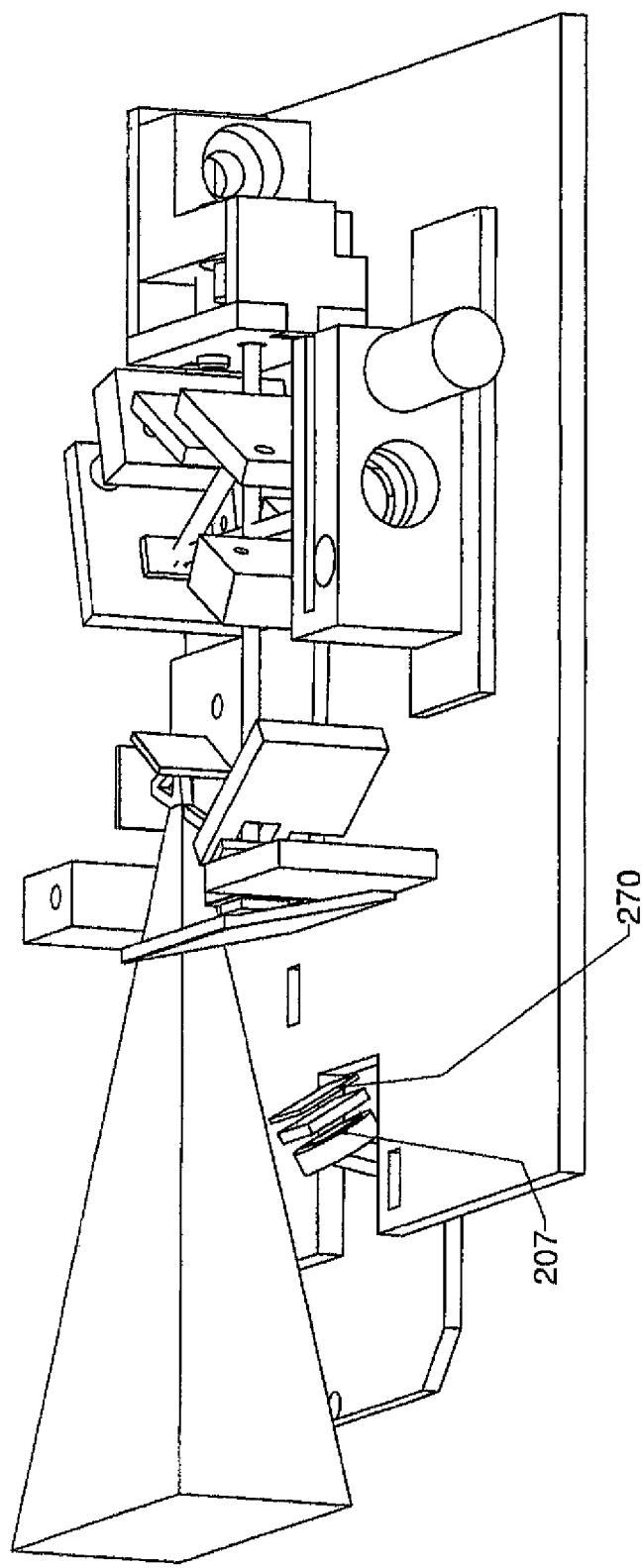
FIG. 8 is a perspective view of the present invention with a polarizing filter and an infrared filter placed in front of the photodiode.

Both embodiments implement 2 photo diodes (hereinafter PDs) and at least two lasers. In addition, depending on the desired result, there can be a polarization film 270, as seen in FIG. 8, placed on the PD, thus further reducing specular reflection. This works particularly well with embodiments of the present invention which include a 740 nm laser and a broad spectrum PD.

Regarding the first embodiment, it is necessary to co-axially align the two lasers. Co-axially aligning the two lasers can be achieved in a multitude of ways. Two methods that have proven to be effective include implementing, either, a dielectric mirror or a polarizer.

The first configuration includes a first laser calibrated to transmit light in the Infrared (hereinafter IF) spectrum, that is 740 nm, and a second laser calibrated to transmit a light in the red color spectrum, that is ≈638 nm. The first configuration, as mentioned above, implements a hot mirror 204 coated with a Dichroic substance, which separates and directs the light onto two separate diodes. This system allows the visible and IR laser reflections in real-time without the use of a memory chip. With this embodiment the 638 nm laser 201 is oriented behind the dielectric mirror. The dielectric mirror is selected so that the 638 nm laser light passed through but the 740 nm is reflected. The 740 nm laser is aimed at the front of the dielectric mirror and is angled and aimed so that the refection of the 740 nm laser is coaxial with the 638 nm laser passing through the dielectric.

In the second configuration, the 638 nm laser is polarized in a first orientation and is placed behind the polarized element. The polarized element is selected so that the first polarized orientation passes through, but the second polarized angle is reflected. The 740 nm is polarized to the second polarized angle and is aimed at the front of the polarized element and is angled and aimed so that the reflection of the 740 nm laser is coaxial with the 638 nm laser passing through the polarized element.

Regarding the second embodiment, the two lasers are multiplexed. It has been noted that the signal received by the 740 nm PD of the present invention is representative of both the veins and the surface topology of the patient. Put another way, the surface of the patient affects the reflected signal. This is not desirable, in that the area of interest is the veins of the patient and not the surface topology of the patient. Thus, by using a second PH for receiving the 630 nm reflected signal, the 630 nm signal (the topology) can be subtracted from the 740 nm signal (topology+veins) yielding a signal that is solely the veins (topology+veins−topology=veins). In this system the microprocessor 250 or state machine circuit, as seen in FIG. 8, can record the reflection from the visible laser and the IR laser can be turned on for one frame, every other frame, or every other scan line. Hence, a new signal would contain a combined laser reflection. The new signal would then be subtracted from the visible signal only, thus leaving the IF signal. The advantage here is that the visible laser does not have to be turned off, which has the benefit of not attenuating the visible light while reading the IF laser reflection.

Other configurations may include a Multi laser array and a LED. First, the Multi laser array will be discussed. In this embodiment a linear array of visible lasers and a linear array of a lasers may replace the single visible laser and single IR laser. With this type of configuration, the linear array of visible lasers and linear array of IR lasers are reflected off a single mirror that oscillates. An advantage of this laser configuration is twofold. First, the mirrors being implemented are less complex. Second, the collection means of the reflected IR light can be obtained by a retro collective mirror. A retro collective mirror is a mirror that has a field of view that corresponds to the array of lasers and moves in concert with the movement of the array of lasers. A characteristic that makes the retro collective mirror ideal for this configuration is the improved signal to noise ratio (SNR).

Evident from the above disclosure, it may be desired to implement one PD 207, as can be seen in FIGS. 1 and 8. In the embodiments that implement one PD, that PD is usually responsive to the 740 nm wavelength but not the 638 nm wavelength. In this manner both lasers can be on at the same time without having the 638 laser couple into the PD. However, the same results can also be achieved via opposite modulation.

In another embodiment the, 638 nm and 740 nm, lasers may be modulated oppositely. In this embodiment the PD will also be responsive to the, 638 nm and 740 nm, laser, but the lasers will be modulated in opposite directions. More specifically, both the lasers can be pulsed on and off at high rates without affecting the apparent quality of the image (638 nm projection), or the quality of the acquired image (the reflections of the 740 nm laser). By synchronizing the two lasers so that the modulation is in opposite directions (the 638 nm on and 740 nm off, followed by, 638 nm off and 740 nm on), the image acquisition circuits (PD and amplifiers, if implemented) can be arranged to ignore signals when the 638 nm laser is on. In this embodiment, the visible 638 nm laser does not interfere at all with the image acquisition apparatus.

All the aforementioned embodiments implemented either single or multiple lasers. It shall be disclosed now that in all aforementioned embodiments a tightly focused LED may replace the lasers. It should be mentioned that this embodiment has limited use in that the resulting projection will not be a collimated laser beam and it will diverge over distance. However, in those limited instances where the distance from the device to the surface is closely held, an appropriate focusing can be obtained.

The present invention also includes a means for gain control. Two possible methods of adjusting the gain of the system are possible. A prior art method of adjusting gain is to fix the 740 nm laser output and to adjust the gain of the photo detection circuitry so as to get an appropriate signal (not too low and not saturated). However, there is complexity in such an adjustment due to the speed requirements of the photo detector gain adjustment. An alternative approach, as in the present invention, is to fix the gain of the photo detection circuitry, as in prior art, but adjust the power output of the 740 nm laser so that an appropriate signal is outputted from the photo detection circuitry (once again not too low, but not saturated). It is much easier to design circuits that adjust the 740 nm lasers due to the extremely high modulation bandwidth of the lasers. For example, the 740 nm laser may be modulated as needed to prevent saturation of the photo detector circuitry. Alternatively, the amplitude of the 740 nm laser can be adjusted to provide appropriate signal out of the photo detection circuitry.

Throughout all the embodiments previously discussed, adjusting the power of either the 638 nm laser, or 740 nm laser, can be achieved by either adjusting the current to the lasers, or alternatively, modulating the lasers on and off at a rapid rate. Regarding modulation, depending upon the duty cycle (pulse-width-modulation), the average laser intensity will be changed. With respect to the visible 638 nm laser, the human eye will integrate the signal and, provided the frequency of the PWM is faster than the eye integration time, the laser will appear dimmer as the on cycle time decreases, and vice versa. The power of the 740 nm laser may be also be adjusted by PWM, this modulation will have the same effect upon the received signal as if the current was decreased to the laser.

Figure 2:
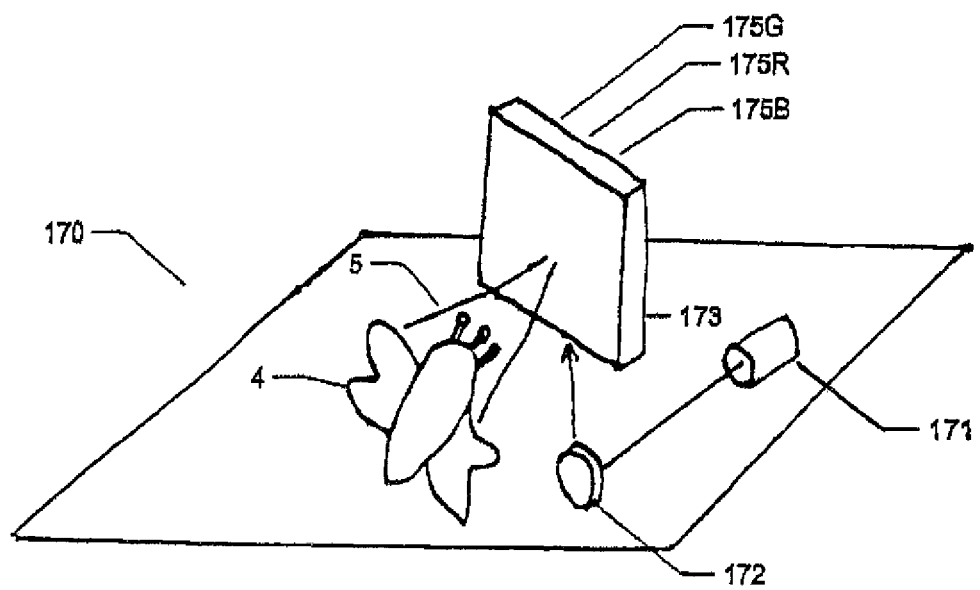
FIG. 2 is a perspective view of a prior art scanning laser based camera (SLBC) that implements a MEMS scanner with three photoreceptors.

The MPH will now be described. FIG. 2 shows a prior art scanning laser-based camera (hereinafter SLBC) 170 of Microvision, Inc. FIG. 17 is taken from Microvision's website: (http://www.microvision.com/technology/imaging-_works.html) dated Jan. 7, 2006, herein incorporated by reference. The SLBC 170 includes a laser source 171 which gets reflected off mirror 172 to a MEMS scanner 173. The MEMS scanner 173 has a reflective surface that can be oscillated in both the X and Y axis. The oscillation of the MEMS scanner 173 is controlled by electronics (not shown) so that the reflected laser beam is moved in a raster pattern. To create a color camera, the laser source is a combination of a red, green and blue laser, thereby forming the color white. Three photodetectors, one responsive to red 175R, one responsive to blue 175B, and one responsive to green 175G are positioned on the SLBC 170 and receive the rastered laser light reflected off object 176. The output of the photodetectors 175R, 175B, and 175B provide an analog rastered image representative of the object 176. The outputs of the photodetectors are converted from an analog signal to a digital signal by D/A converters (not shown). A controller (not shown) determines the instantaneous rastered laser light position and converts that to an appropriate pixel location. The controller then writes the digitized RGB values to an appropriate pixel memory location. By repeating this step for each pixel location, a digitized version of the object is stored in memory. Each raster sweep of the field of view 4 results in a new image being stored. By sweeping at video rates, video images can be captured.

A publication in *Laser Focus World*. December 2004, authored by Chris Wiklot entitled *"Display technology spawns laser camera"*, herein incorporated by reference, describes the SLBC of FIG. 2 in even greater detail.

Figure 4:
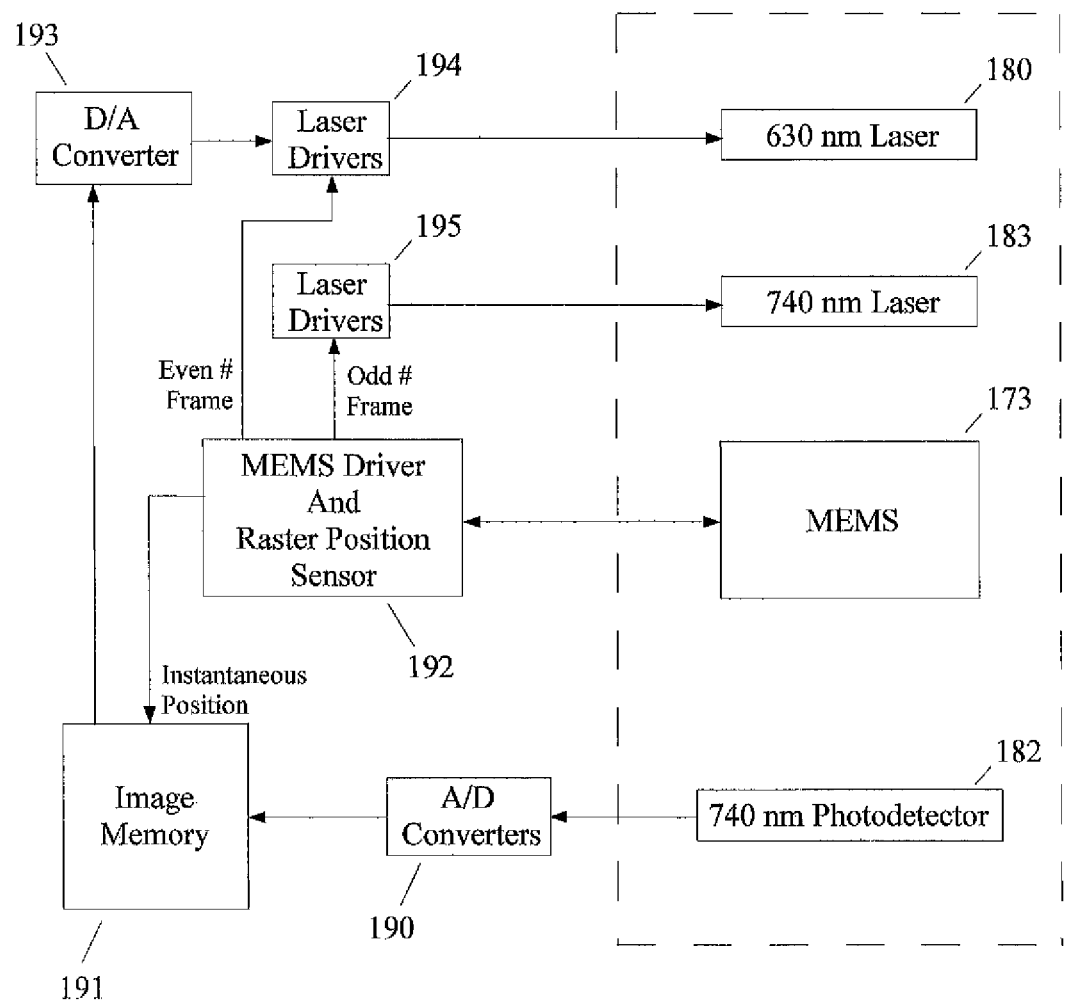
FIG. 4 is a functional block diagram that illustrates the present invention operating in Alternating Frame Mode (AFM).
Figure 5:
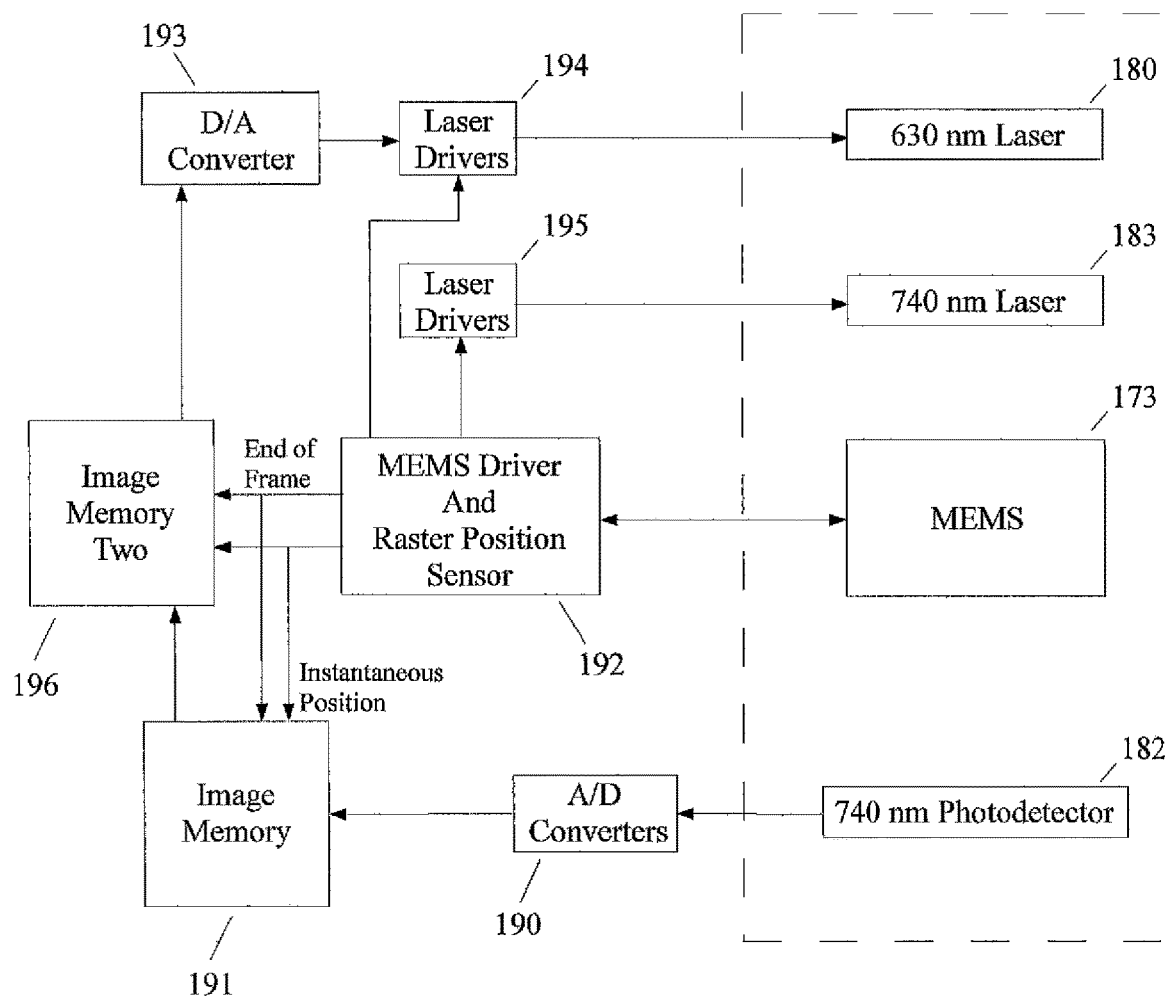
FIG. 5 is a functional block diagram that illustrates the present invention operating in Dual Buffer Mode (DBM).
Figure 6:
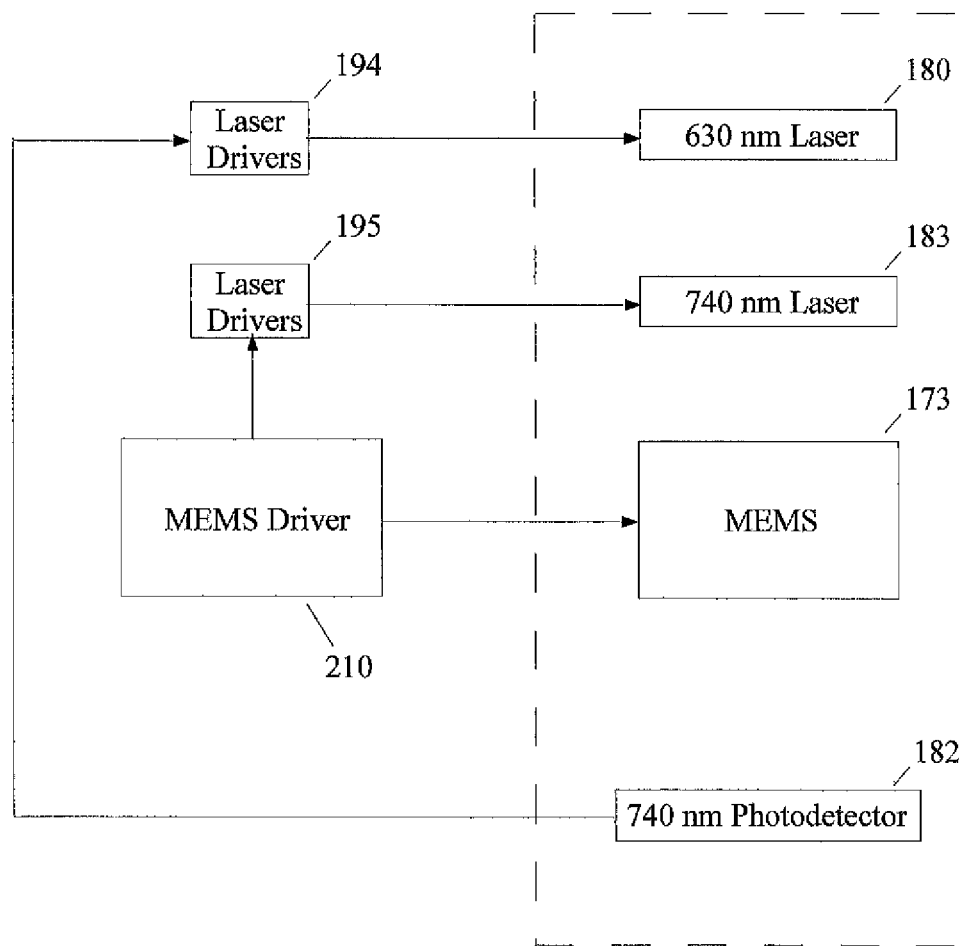
FIG. 6 is a functional block diagram that illustrates the present invention operating in Real-Time Mode (RTM).

Drawing one's attention to FIGS. 4-6 are three different modes of operation that the present invention may be used, a brief description of each mode of operation follows.

A first mode of operation which will be referred to hereinafter as an "Alternating Frame Mode" (AFM) may be seen in FIG. 4. In the AFM mode, an electronic block 192 for driving the MEMS driver and for sensing the position of the raster scanner is provided 192. This block generates the signals required to drive the MEMS scanner 173 in a raster pattern, and also determines the exact instantaneous location of the MEMS scanner and communicates this information to an image memory 191. This electronic block 192 also generates output signals and indicates whether the current frame (a frame is a complete raster of the field of view) is an odd number Frame 1 or an even number Frame 2 (essentially the two signals are opposite and switch polarity every other frame). The operation is as follows. The MEMS 173 is driven in a raster pattern. The first full frame after achieving a stable raster pattern will be identified as an odd number frame and the laser driver 195 for the 740 nm laser 183 is turned on for the entire frame. During this time the laser drive 194 for the 630 nm laser is turned off. The light from the 740 nm is absorbed by the veins in a patient's body and reflected by the skin of the patient, thus forming a contrasted image that is then sensed and converted into an analog signal by 740 nm photodetector 182. The analog signal is then passed through an A/D converter 190 which outputs a digital representation to image memory 191. Image memory 191 also receives instantaneous position information from the electronic block 192, and based upon such information, the digital representation is stored in a memory location corresponding to a particular pixel. This is repeated for each pixel within the odd frame. Upon completion of the odd frame, the image memory contains the image of the veins within the field of view of the MPH. During the even number frame, the laser driver 195 to the 740 nm laser is turned off. The data in the image memory 191 is read out as a function of the instantaneous position information provided by the electronic block 192 and provided to a D/A converter 193 which outputs an analog signal to laser drive 194 which drives the 630 nm laser. In this manner, the image that was stored in the odd number frame is projected by the 630 nm laser 180 in the even number frame. In this manner, the veins that are in the field of view become visible to the practitioner.

A second mode of operation is shown in FIG. 5. This mode shall be referred to hereinafter as the "Dual Buffer Mode" (DBM). In the DBM, a second image memory called image memory two 196 is added. In the DBM, the laser driver to the 740 nm laser is turned on for every frame and in each frame the image of the veins is captured and stored in image memory 191 exactly as described previously in the AFM mode. However, in this case the electronic block 192 provides an end of frame indication to both image memory two 196 and image memory 191 which causes the entire image stored in the image memory 191 to be transferred to image memory two 196 during the blanking time of the raster scan (the time after the raster scan is completed but before the next raster scan starts). During the next frame, the contents of image memory two 196 is then projected by the 630 nm laser onto the field of view. In this manner, the visible image projected is always one frame behind the actual image captured. Provided the frame rate is fast enough, this delay should not be apparent to the practitioner. Frame rates in excess of 30 frames per second can easily be achieved with the MEMS scanner provided herein.

The DBM mode is advantaged as compared to the AFM in that the visible laser is on every frame, and therefore is twice as bright. However, the AFM mode is advantaged in that it only requires a single memory buffer and therefore is more cost effective than the DBM mode.

A third mode of operation is illustrated in FIG. 6. This mode shall be referred to hereinafter as the "Real Time Mode" (RTM). In the RTM the MEMS 173 is driven in a raster pattern by a MEMS driver 210. The laser driver 195 to the 740 nm laser is turned on all the time. The reflected light is received by the 740 nm photodetector 182 and the analog signal produced is connected to the laser driver 194 for the 630 nm laser 180. In this manner the red laser 180 projects nearly instantaneously the signal that is being received by the photodetector 182. The only delay is dictated by the speed of the photodetector and the laser drive 194 circuitry. Accordingly, there is no need for an image memory buffer and associated D/A converters and A/D converters. Further, since the image is never stored, there is no requirement to sense the instantaneous position of the laser for the purpose of clocking the image into memory or for projecting the visible image. In fact, in this RTM, the raster pattern does not need to be as steady and repeatable as that of the other modes, thereby possibly decreasing the complexity and cost of the MEMS and associated drive circuitry.

Drawing one's attention now to FIG. 1 is a preferred embodiment 200 of a MPH the present invention. This embodiment replaces the MEMS scanner with a two dimensional mirror. One such two dimensional mirror is provided by Fraunhofer IPMS. In a press release dated Jan. 3, 2005 they described a two dimensional mirror as follows:

"Projection devices based on laser scanning are a very interesting alternative to matrix displays. A modulated laser and a deflection unit are necessary. Using micro scanning mirrors for implementing the laser beam deflection in a projection device has many advantages. In particular, micro scanning mirrors, which operate resonantly in both directions, enable the development of systems with very small size, high deflection angles with low voltage and low power consumption. The presented demonstrator uses a commercial laser module and a 2D micro scanning mirror operated with deflection frequencies of 9.4 kHz and 1.4 kHz. The device uses both axes to perform a sinusoidal oscillation, which causes a beam trajectory that describes a Lissajous pattern with high density, instead of the usually implemented linear scanning. Therefore, mirrors with low ratio of horizontal and vertical deflection frequency can be used. This kind of micro scanning mirrors can be fabricated easily and cost effective. The control circuit is developed with an FPGA and provides a resolution of 256.times.256 monochromatic pixels. Programmable counters are used for generating the mirror driving signals and for determining the beam position. Mirror excitation and image synchronization work without feedback loop. This means, no complicated optical or electronic synchronization techniques are needed. This simplifies micro scanning mirror and control circuit and enables low cost production. Applications of the projection device are displays, laser marking and laser exposure."

In the RTM of FIG. 6, the two-dimensional mirror of Fraunhofer IPMS creates a Lissajous pattern with high density instead of the raster pattern. The visible laser will simply follow nearly instantaneously the image detected by the 740 nm laser detector.

The MPH 200 may also include two laser sources. A first laser source 201 having a wavelength in the visible light spectrum, preferably ≈632 nm, and a second laser 202 having a wavelength preferably ≈740 nm, that is IR. Lasers 201 and 202 may be any suitable lasers known in the art.

Combiner 203 may have at least one bounce mirror. In a preferred embodiment there can be two bounce mirrors, 203a and 203b. In the preferred embodiment combiner 203 may also include a dielectric coated mirror 204. Mirror 204 may be any suitable type of dielectric coated mirror known in the available art. In a preferred embodiment mirror 204 was coated with a material that reflects IR and transmits other wavelengths. As mentioned above, the embodiment as depicted in FIG. 1 replaces the MEMS scanner with a two dimensional scanning mirror 205, such as the type provided by Fraunhofer IPMS. With this embodiment there can also be a collection mirror 206, and at least one PD 207.

Figure 7:
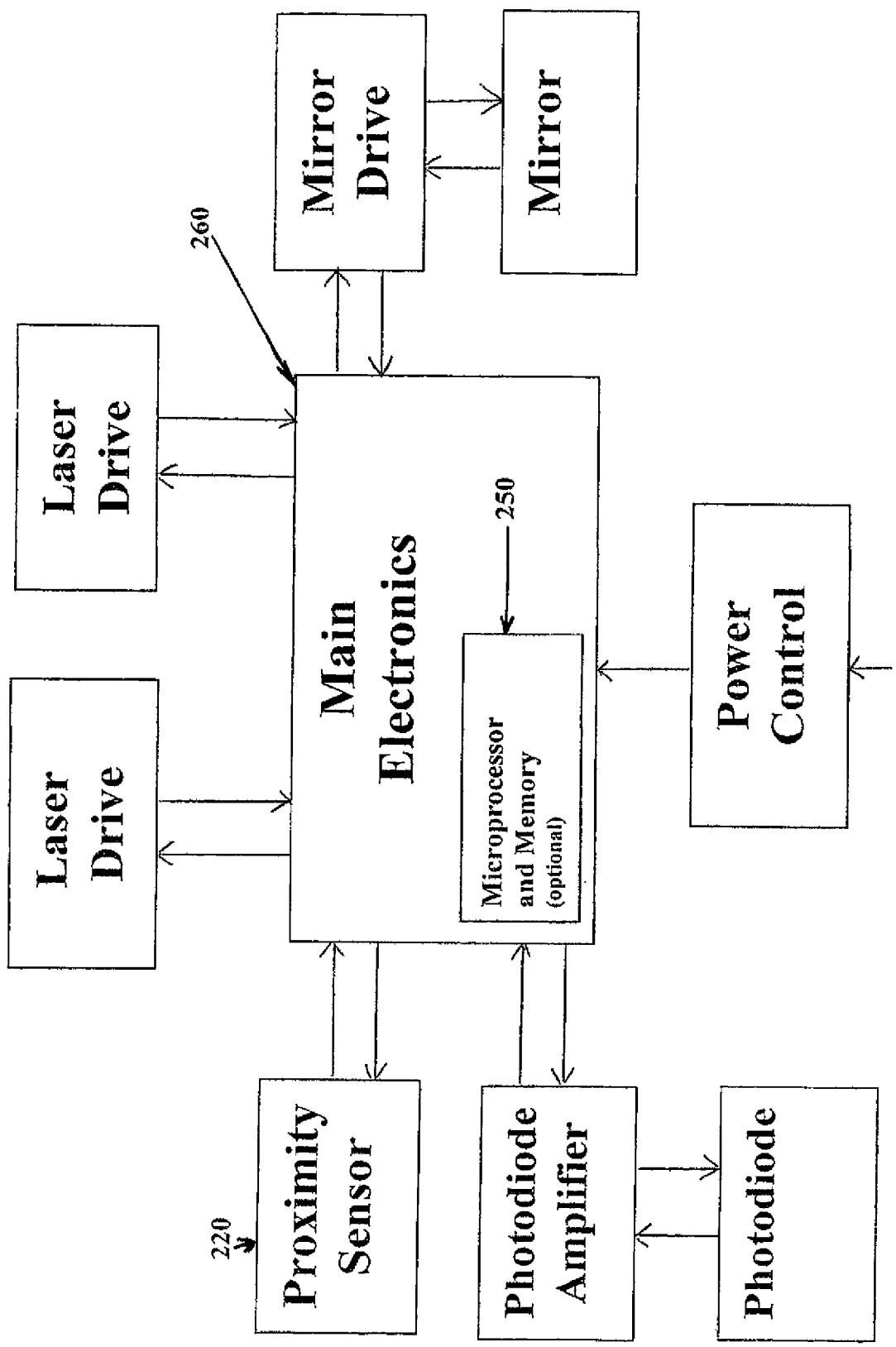
FIG. 7 is a functional block diagram that illustrates the interfaces between different components of the present invention.

In normal operation, the embodiment as depicted in FIG. 1 operates as previously discussed, that is, in any of the three operating modes; however, it performs optimally in RTM. In yet another embodiment the lasers can be multiplexed, in which case the visible laser would not have to be turned off. In this embodiment all components would function in a similar manner as previously mentioned embodiments. However, the microprocessor or state machine 250 in this embodiment, as seen in FIG. 7, can record the reflection of the visible laser 201 and then the IR laser 202 can be turned on for any interval time duration, and combined with the visible laser. Thus, the resultant beam 240 would be a combination of both lasers. Beam 240 would be then subtracted from the previously recorded visible laser. The advantage here is that the projected visible laser would not be reduced by turning off the visible laser to read the infrared laser reflection.

In another embodiment of the present invention there can be what is known in the art as a "hot mirror". Mirror 206 is preferably coated with a dichroic coating. This acts as a beam splitter. In normal operation mirror 206 will direct the light onto two separate PDs. With this type of embodiment all other previously mentioned components may operate in the same manner. In normal operation laser 202 will transmit IR light 220 which will bounce off of bounce mirror 203*a*. At which time laser 202 will begin to transmit light 221 at 632 nm. Light 221 will pass through dielectric coated mirror 204 and light 220 will reflect of mirror 204, resulting in a beam of light 222 that is a combination of both lights, as seen in FIG. 1. Beam 222 will then be reflected of bounce mirror 203*b*. The angle at which beam 222 is reflected will depend on the angle at which bounce mirror 203*b* is placed. This will be determined by the manufacturer's design requirements. Once reflected off bounce mirror 203*b* beam 222 will be projected onto the area of interest, that is, the area where the vein is located, via two dimensional scanning-mirrors 205. The projected beam 222 will then be collected by collection mirror 206. After which, collected beam will then be passed through hot mirror 206 to separate and direct beam 222 onto two PDs 207. This embodiment compares the visible light and the IR laser reflections in real-time, without a memory chip.

Figure 3:
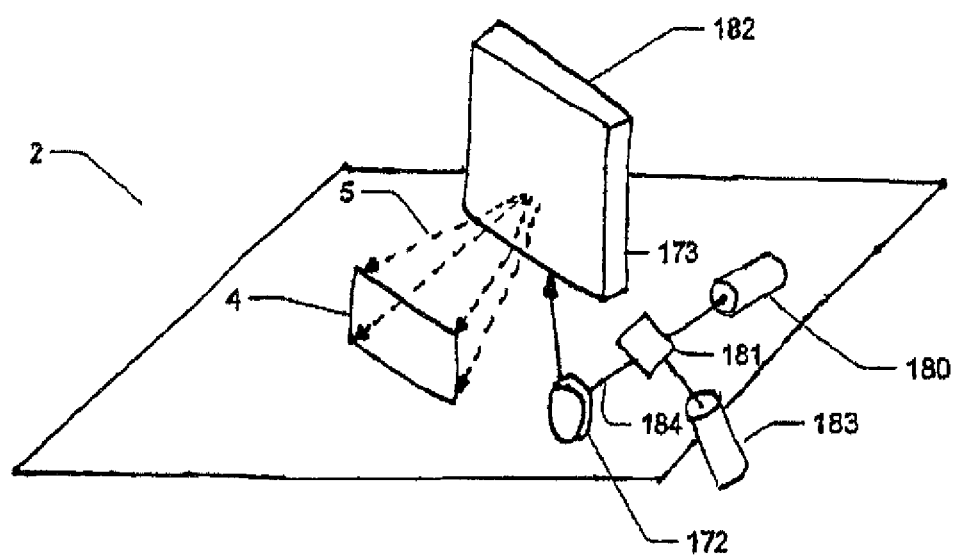
FIG. 3 is a perspective view of the Vein Enhancer of the present invention with a MEMS scanner that implements two photodiodes.

Other embodiments may implement a MEMS scanner, as seen in FIG. 3, to perform the same function as the two dimensional mirrors. This will depend on economic as well as practicable considerations.

Furthermore, there can be any array of polarizing filters and/or infrared filters located between the collection mirror and the photodiode, as seen in FIG. 8.

In the embodiments herein the visible light transmitted was a red laser. However, any visible color or combination of color could be transmitted. For example, three laser RGB could be utilized to transmit full color images onto the field of view.

While in the embodiments herein a single two-dimensional mirror which moves in two axis was used for steering the beam, other beam steering arrangements could be used. For example, the outgoing laser beams can be bounced first off a one dimensional high speed scanning mirror and then off a second lower speed mirror scanning in the opposite direction. There are many other methods known to those skilled in the art for creating raster and other scanned laser patterns.

While many of the embodiments described herein utilized vial holders with needles, there are many other medical procedures which need to view the veins. The invention is not intended to be limited to devices which attach to vial holders.

As various changes could be made in the above constructions without departing from the scope of the invention, it is intended that all matter contained in the above description shall be interpreted as illustrative and not in a limiting sense. In the view above it will be seen that several objects of the invention are achieved and other advantageous results attained, as defined by the scope of the following claims.

We claim:

1. A portable hand-held miniature vein enhancer, for imaging subcutaneous blood vessels of a target area, said vein enhancer comprising:
a first laser configured to emit a beam of light at a first wavelength;
one micro scanning mirror configured to move about two axes to scan said first wavelength of light from said first laser onto the target area in a non-repeated and non-diffuse pattern;
one photo detector responsive to said first wavelength of light and associated photodetector circuitry, said one photo detector configured to receive said first wavelength of light reflected from the target area, said reflected light comprising a contrasted image formed by differential absorption of said first wavelength of light by the target, being amplitude modulated according to differential amounts of absorption and reflection between one or more subcutaneous blood vessels and surrounding tissue therein; said one photo detector configured to output a signal representing said contrasted image;
a second laser configured to emit a beam of visible light at a second wavelength;
one or more fixed mirrors, at least a first one of said one or more fixed mirrors comprising optical characteristics configured to cause either reflection of said first wavelength of light and transmission of said second wavelength of light, or transmission of said first wavelength of light and reflection of said second wavelength of light;
wherein said first laser, said second laser, and said first fixed mirror are positioned to combine said beam of light from said first laser and said beam of light from said second laser using said first fixed mirror, to form a single coaxial beam of laser light; and
wherein said second laser is configured to receive and use said signal from said one photodetector to emit said beam of visible light, for said micro scanning mirror to scan said visible light in said co-axial beam to result in projection of said contrasted image substantially instantaneously, and in focus on the target area for imaged blood vessels in said projection of said contrasted image to overlie the subcutaneous blood vessels therein, regardless of a distance of said miniature vein enhancer from the target area.

2. The portable hand-held miniature vein enhancer according to claim 1 wherein said substantially instantaneous projection of said contrasted image is dependent upon only a speed of said photo detector and a speed of said second laser.

3. The portable hand-held miniature vein enhancer according to claim 2 further comprising a hand-holdable housing configured to receive and support said one photo detector and said one micro scanning mirror, and to support said positioned first laser, second laser, and first fixed mirror; said housing further configured to permit single-handed lifting and use of said miniature vein enhancer during said in-focus projection of said contrasted image onto the target area.

4. The portable hand-held miniature vein enhancer according to claim 3 wherein said micro scanning mirror is configured to scan about a first axis of said two axes at a deflection frequency of 9.4 kHz, and to scan about a second axis of said two axes at a deflection frequency of 1.4 Hz.

5. The portable hand-held miniature vein enhancer according to claim 3 wherein said micro scanning mirror is configured to scan at its natural resonance frequency to minimize power usage.

6. The portable hand-held miniature vein enhancer according to claim 3, further comprising a cap; and wherein said hand-holdable housing comprises a holder configured to receive a battery; said cap configured to be releasably secured to said housing to provide access to said battery holder.

7. The portable hand-held miniature vein enhancer according to claim 3 further comprising a sensor, and wherein said first laser is turned on only when said sensor detects the target area.

8. The portable hand-held miniature vein enhancer according to claim 3 wherein said first wavelength is in the range of 700 nm to 1000 nm; and wherein said second wavelength comprises a red color.

9. The portable hand-held miniature vein enhancer according to claim 1 further comprising means for controlling gain, for preventing saturation of said photo detector circuitry.

10. A portable hand-held miniature vein enhancer for imaging subcutaneous blood vessels of a target surface, said vein enhancer comprising:
   a first laser configured to emit a beam of light at a first wavelength;
   one or more movable mirrors configured to selectively move to cause said first wavelength of light from said first laser to be transmitted onto the target surface in a non-diffuse pattern;
   one or more photo detectors responsive to said first wavelength of light, said one or more photo detectors configured to receive said first wavelength of light reflected from the target surface, said reflected light comprising a contrasted image formed by said reflected light from the target surface being amplitude modulated according to differential amounts of absorption and reflection between one or more subcutaneous blood vessels and surrounding tissue therein; said one or more photo detectors configured to output a signal representing said contrasted image;
   a second laser configured to emit a beam of visible light at a second wavelength;
   one or more fixed mirrors, at least a first one of said one or more fixed mirrors comprising optical characteristics configured to cause either reflection of said first wavelength of light and transmission of said second wavelength of light, or transmission of said first wavelength of light and reflection of said second wavelength of light;
   wherein said first laser, said second laser, and said first fixed mirror are positioned to combine said beam of light from said second laser with said beam of light from said first laser using said first fixed mirror, to form a single coaxial beam of light; and
   wherein said second laser is configured to receive and use said signal from said one or more photo detectors to emit said beam of visible light, for said one or more moving mirrors to scan said visible light of said single coaxial beam to result in projection of said contrasted image substantially instantaneous, to be in-focus on the target surface for the imaged blood vessels in said projection of said contrasted image to overlie the subcutaneous blood vessels therein, regardless of a distance of said vein enhancer from the target surface.

11. The portable hand-held miniature vein enhancer according to claim 10 wherein a delay causing said projection to be substantially instantaneous comprises a delay resulting from a speed of said one or more photo detectors and a speed of said second laser.

12. The portable hand-held miniature vein enhancer according to claim 11 further comprising a hand-holdable housing configured to receive and support said one or more photo detectors and said one or more movable mirrors, and to support said positioned first laser, second laser, and first fixed mirror; said hand-holdable housing further configured to permit single-handed lifting and use of said miniature vein enhancer during said in-focus imaging of the target area.

13. The portable hand-held miniature vein enhancer according to claim 12 wherein said one or more movable mirrors configured to selectively move comprises a mirror arrangement selected from the group of mirror arrangements consisting of:
   a MEMS scanner;
   a single moving mirror capable of oscillations about two axes to produce said pattern; and
   a first moving mirror and a second moving mirror, said first moving mirror configured to move about a first axis, said first moving mirror being angled to reflect said single coaxial beam of laser light to said second moving mirror, said second moving mirror configured to move about a second axis, said coaxial beam being reflected from said second moving mirror toward the target surface, said motion of said first and second mirrors cooperating to move to produce said pattern.

14. The portable hand-held miniature vein enhancer according to claim 13 further comprising a mirror drive subsystem, said mirror drive subsystem configured to cause said selective movement of said one or more movable mirrors at a frequency to synchronize said first and second mirrors; said mirror drive subsystem comprising one or more microprocessors configured for control thereof.

15. The portable hand-held miniature vein enhancer according to claim 14 wherein said repeated pattern of light comprises a pattern from the group of patterns consisting of: a raster pattern; a collapsing oval pattern; a collapsing circle pattern; and a Lissajous pattern.

16. The portable hand-held miniature vein enhancer according to claim 15 wherein said raster pattern is generated by said first moving mirror oscillating at a higher frequency than said second moving mirror.

17. The portable hand-held miniature vein enhancer according to claim 14 wherein said one or more movable mirrors are driven by said subsystem at a natural resonance frequency to minimize power usage.

18. The portable hand-held miniature vein enhancer according to claim 14 further comprising a proximity sensor, and wherein said first laser is turned on only when said proximity sensor detects the target surface.

19. The portable hand-held miniature vein enhancer according to claim 14 wherein said first wavelength of laser light is a wavelength in the range of 700 nm to 1000 nm, and said second wavelength of laser light comprises a red color.

20. The portable hand-held miniature vein enhancer according to claim 10 further comprising means for controlling gain of said first laser.

21. A portable hand-held miniature vein enhancer, for use in imaging subcutaneous blood vessels of a target surface, said vein enhancer comprising:
   a first laser configured to emit a beam of light at a first wavelength;
   one mirror configured to selectively move about two axes to scan said first wavelength of light from said first laser onto the target surface in a non-repeated non-diffuse pattern;
   one or more photo detectors responsive to said first wavelength of light and associated photodetector circuitry, said one or more photo detectors configured to receive said first wavelength of light being reflected from the target surface, said reflected light comprising a contrasted image being formed by said reflected light from the target surface being amplitude modulated according to differential amounts of absorption and reflection between one or more subcutaneous blood vessels and surrounding tissue therein; said one or more photo detectors configured to output a signal representing said contrasted image;

a second laser adapted to emit a beam of visible light at a second wavelength;

a combiner;

wherein said first laser, said second laser, and said combiner are positioned to combine said beam of light from said first laser and said beam of light from said second laser using said combiner, to form a single coaxial beam of laser light; and wherein said second laser is responsive to said signal output by said one or more photo detectors, said second laser thereby configured to project said contrasted image substantially instantaneously, using said one mirror, to be in-focus on the target surface for the imaged blood vessels in said projection of said contrasted image to overlie the subcutaneous blood vessels therein, regardless of a distance of said vein enhancer from the target surface.

22. The portable hand-held miniature vein enhancer according to claim 21 wherein said substantially instantaneous projection of said contrasted image is dependent upon only a speed of said photo detector and a speed of said second laser.

23. The portable hand-held miniature vein enhancer according to claim 22 further comprising a hand-holdable housing configured to receive and support said one or more photo detectors and said one mirror, and to support said positioned first laser, second laser, and combiner; said hand-holdable housing further configured to permit single-handed lifting and use of said miniature vein enhancer during said in-focus imaging of the target area.

24. The portable hand-held miniature vein enhancer according to claim 22 wherein said one mirror is configured to scan about a first axis of said two axes at a deflection frequency of 9.4 kHz, and to scan about a second axis of said two axes at a deflection frequency of 1.4 Hz.

25. The portable hand-held miniature vein enhancer according to claim 21 further comprising means for controlling gain of said first laser, for preventing saturation of said photo detector circuitry.

* * * * *